(12) United States Patent
Vroblesky (10) Patent No.: US 7,430,929 B1
(45) Date of Patent: Oct. 7, 2008

(54) PORE WATER SAMPLER FOR LONG-TERM MONITORING OF GROUND WATER

(75) Inventor: Don A. Vroblesky, Columbia, SC (US)

(73) Assignee: The United States of America, as represented by the Secretary of the Interior, Washington, DC (US)

( * ) Notice: Subject to any disclaimer, the term of this patent is extended or adjusted under 35 U.S.C. 154(b) by 315 days.

(21) Appl. No.: 11/401,011

(22) Filed: Apr. 6, 2006

(51) Int. Cl.
*G01N 1/00* (2006.01)
(52) U.S. Cl. .................................. 73/863.23; 73/864.74
(58) Field of Classification Search ........................ None
See application file for complete search history.

(56) References Cited

U.S. PATENT DOCUMENTS

| | | | |
|---|---|---|---|
| 4,923,333 | A | 5/1990 | Timmons |
| 5,000,051 | A | 3/1991 | Bredemeier |
| 5,889,217 | A * | 3/1999 | Rossabi et al. ............ 73/864.74 |
| 6,742,405 | B2 | 6/2004 | Hubbell et al. |
| 6,962,660 | B2 * | 11/2005 | Wybo .......................... 210/315 |
| 6,978,688 | B2 | 12/2005 | Engebretson |
| 2004/0089079 | A1 * | 5/2004 | Engebretson ............ 73/863.23 |

OTHER PUBLICATIONS

U.S. Appl. No. 10/767,496, filed Jan. 28, 2004, Vroblesky.
Vroblesky, D.A., "User's Guide for Polyethylene-Based Passive Diffusion Bag Samplers to Obtain Volatile Organic Compound Concentrations in Wells: Part 1: Deployment, Recovery, Data Interpretation, and Quality Control and Assurance," *U.S. Geological Survey Water-Resources Investigations Report 01-4060*; 2001; pp. 1, 3, and 4; <http://sc.water.usgs.gov/publications/pdfs/WRIR01-4060.pdf>.
"User's Guide for Polyethylene-Based Passive Diffusion Bag Samplers to Obtain Volatile Organic Compound Concentrations in Wells: Part 2: Field Tests," *U.S. Geological Survey Water-Resources Investigations Report 01-4061*, Don A. Vroblesky ed.; 2001; pp. cover page, I, A-3, and A-4; <http://sc.water.usgs.gov/publications/pdfs/WRIR01-4061.pdf>.
Vroblesky, D.A., Petkewich, M.D., and Campbell, T.R., "Field Tests of Diffusion Samplers for Inorganic Constituents in Wells and at a Ground-Water-Discharge Zone," *U.S. Geological Survey Water-Resources Investigations Report 02-4031*; 2002; pp. 1-4; <http://sc.water.usgs.gov/publications/pdfs/WRIR-02-4031.pdf>.
"Gravel Pack Screens," Baker Hughes Inc., 3900 Essex Lane, Suite 1200, Houston, TX 77027-5177, 7 pp. <http://www.bakerhughesdirect.com/cgi/hello.cgi/BOT/public/thru_tubing/pdf/scs_p.31_37.pdf>, dated downloaded Apr. 2006.

* cited by examiner

*Primary Examiner*—Robert R Raevis
(74) *Attorney, Agent, or Firm*—C. Joan Gilsdorf (57) ABSTRACT

A method and device for sampling pore water, including an elongated tubular outer body having a grid framework forming multiple perforations throughout the entire outer body. The grid framework surrounding the perforations has raised and beveled sides. An elongated, perforated tubular inner body is contained within the outer body. The inner body has a diameter less than a diameter of the outer body, which forms a cavity between the inner body and the outer body. The cavity is filled with an inert granular filler material. A first outer cap and a second outer cap cover respective ends of the outer body. A coupling is placed in fluid communication with the inner body and protrudes through the first outer cap. A tube is attached to the coupling protruding through the first outer cap to transfer a water sample to a sample collection site.

20 Claims, 10 Drawing Sheets

PORE WATER SAMPLER FOR LONG-TERM MONITORING OF GROUND WATER

STATEMENT OF GOVERNMENT INTEREST

The invention described herein may be manufactured and used by or for the Government of the United States of America for government purposes without the payment of any royalties therefore.

BACKGROUND

Bibliographic details of the publications and the web sites numerically referred to in this specification are collected at the end of the description.

The present invention is directed, in general, to liquid sampling devices and, more particularly, to the monitoring of solutes in pore water beneath surface water.

In most cases of ground water contamination discharging to surface water, the surface water body is considered to be the "point of contact" where there is a potential for contact of the contamination with flora or fauna. Because wells typically are not practical to install or sample beneath surface water, wells on land typically are considered to be the "point of compliance." The point of compliance is the point at which the concentrations of contaminants must meet regulatory levels. However, numerous studies have shown that substantial contaminant degradation can take place in pore water in the immediate vicinity of the ground water discharge to surface water. Thus, the concentrations at the point of compliance often may substantially overestimate the actual discharge concentrations.

The ability to routinely monitor the actual discharge concentrations can potentially allow a government facility, for example, to move the point of compliance from wells to the pore water beneath the surface water body. This will take advantage of the accelerated contaminant degradation in sediment near the discharge zone and allow the facility to more rapidly achieve compliance concentrations required by regulatory agencies in ground water prior to the point of contact. If an onshore well contains contaminant concentrations in excess of regulatory action limits and a pore water sampler shows that concentrations have declined to an acceptable range prior to discharge to surface water, substantial cost savings can be achieved by the closing of the monitoring site.

There is strong interest on the part of the U.S. Department of Defense (DoD) to develop the ability to monitor contaminant discharge to surface water. For example, programs are underway to design an extensive environmental monitoring system at Marine Corps Base Camp Lejeune and surrounding environs in east central North Carolina as part of an effort to address military and other impacts on the New River Estuary in North Carolina. In addition, the DoD has requested the development of technology that will allow the long-term monitoring of chlorobenzene contamination in pore water beneath surface water at the Naval Air Station in Corpus Christi, Tex. Existing technology is inadequate to perform this task.

Existing technology for sampling contaminants in pore water beneath surface water includes diffusion samplers. Diffusion samplers are polyethylene bags or other material filled with water or sorbent that are used in wells or other environments to passively sample volatile organic compounds (VOCs) (see Vroblesky and Hyde [8], Karp [4], and Imbrigiotta et al. [2]). Diffusion samplers include passive diffusion bag (PDB) samplers that have been widely used. A user's guide for PDB samplers has been published (see Vroblesky [10] and [11]). Passive vapor samplers have been developed for sampling beneath surface water (see Church et al. [1] and Vroblesky [9], [12], and [13]). Diffusion samplers for inorganic constituents have also been used (see Vroblesky et al. [14] and [15]). Nylon-screen diffusion samplers have been used to sample interstitial pore waters in wetlands sediment (see Paludan and Morris [7]).

Most diffusion samplers, including the ones mentioned above, are not rechargeable. In other words, the non-rechargeable diffusion samplers are one-time use instruments that require removal for recovery and replacement of a new sampler. The specific sampling point cannot be resampled for confirmation. Thus, non-rechargeable diffusion samplers have limited value for long-term monitoring of a specific sampling point.

A rechargeable dialysis pore water sampler has been tested (see Jacobs [3]), but this type of sampler must be refilled with deionized, deoxygenated water. Creating deoxygenated water can be time consuming and troublesome. A pore water sampler is needed that does not require refilling with any kind of water, and that allows samples to be collected from the same location indefinitely, assuming sufficient time elapses between sampling events for the ambient water to return to pre-pumped conditions.

A broad variety of other diffusion-type samplers are available and have been reviewed in a recent journal article (see Namieńsnik et al. [5]).

Wells sometimes are installed in surface water bodies to monitor pore water concentrations, but wells are limited in their application. Wells require a surface expression, such as a standpipe, that may be subject to disturbance by floating objects or currents. Moreover, bottom sediment is often fine grained, necessitating the need for a sand pack or other sediment-filtering material surrounding the well screen.

Well screens with prepacked sand packs are widely available. Examples can be found at the websites of the following companies: Geoprobe Systems [16], Johnson Screens (India) Ltd. [17], Weatherford International Ltd. [18], and Baker Hughes Inc. [19]. These well screens are designed to be attached to well pipe that extends below land surface. The designs are available as wire-wrapped and slotted pipe and typically have a sand pack attached to them that is held in place by a stainless steel screen. The existing prepacked well screens are designed to be attached to well casing and, thus, are not applicable to monitoring pore water beneath surface water bodies.

Some prepacked screens are designed for oilfield use and are very complex. For example, see the prepacked system shown on page 5 of the Schlumberger Limited website (see Schlumberger Limited [20]).

Some prepacked well screens are expensive because stainless steel pipes are used. An example can be seen at the website of Johnson Screens (India) Ltd. [17]. The strength and durability provided by stainless steel pipes are not needed for the less pressurized environment of the bottom-sediment pore water. Although some prepacked well screens have a small-diameter pipe and are constructed of mostly plastic material, such as the screens available from Geoprobe Systems (see Geoprobe Systems [16]), the prepacked sand in these wells is held in place by a stainless steel well screen. The stainless steel is needed because a less expensive material, such as nylon mesh, is not durable enough to withstand deployment abrasion. However, some of the parameters of interest in pore water investigations may be adversely affected by the stainless steel. Stainless steel in contact with water can generate hydrogen (see Bjerg et al. [6]). Because hydrogen is of great interest in microbial investigations of ground water, the potential for stainless steel to produce artificially high hydrogen concentrations makes stainless steel an undesirable option for this type of sampling. In addition, stainless steel is not recommended for metals sampling (see Ministry of Environment [21].) A pore water sampler is needed that is not constructed of stainless steel.

Some existing prepacked screens are designed to sample aquifer sediment, which typically consists of sands or gravels. However, bottom sediment beneath surface water bodies usually is substantially different than aquifer sediment. Bottom sediment often is fine grained and in quiescent water can consist of a substantial amount of forest detritus. This detritus can consist of partially decomposed leaves, which have a sheet-like character. A single leaf, when pulled against a screen or a smooth, slotted surface (such as the surface of the lysimeter described in U.S. Pat. No. 4,923,333), can wrap around and block a large amount of the screen opening, cutting off flow. A pore water sampler is needed that is able to counteract the potential for leaf debris to blanket and obstruct large parts of the screen.

Typical prepacked screens used in oil technology are longer than 10 feet. Small-diameter prepacked screens for ground water monitoring are available in 3-feet and 5-feet lengths. However, substantial changes in water chemistry can take place in bottom-sediment pore water over distances much less than 3 feet. Therefore, a smaller sampler is needed for this environment.

Thus, a pore water sampler is needed that is small in size (less than 3 feet), is constructed mainly of plastic or polymers, does not need to be refilled, and can counter the potential blockage effects of sheet debris.

SUMMARY

It is an aspect of the present invention to provide a stand-alone apparatus that can be used for long-term monitoring of solutes in pore water beneath surface water.

Another aspect of the present invention is to provide an apparatus for pore water sampling that is self filling with ambient formation water and that does not need to be refilled with deionized, deoxygenated water after each sample is collected.

Another aspect of the present invention is to provide an apparatus for pore water sampling that is constructed of plastics rather than stainless steel.

Another aspect of the present invention is to provide an apparatus for pore water sampling that can reduce or eliminate blockage of the outer surface of the apparatus.

These and other aspects are achieved according to the present invention by providing a method and apparatus for pore water sampling. A pore water sampler with a pre-packed screen is buried in bottom sediment beneath surface water in an area where pore water contamination is known or suspected. Tubing connects the sampler to the shore. The sampler is constructed almost entirely of plastic and polymers, making it substantially less expensive than prepacked screens constructed of stainless steel. The sampler also has no stainless steel in intimate contact with water movement, minimizing potential chemical effects that could be associated with stainless-steel well screens. The outer layer of the sampler is a rigid, plastic pipe having perforations throughout the entire outer layer. A raised framework surrounding each perforation counters the potential blockage effects of sheet debris, such as leaf matter.

According to an embodiment of the present invention, there is provided a device for sampling water, including an elongated tubular outer body having a grid framework forming a plurality of perforations throughout the entire outer body, the grid framework surrounding the perforations having raised and beveled sides. An elongated, perforated tubular inner body is contained within the outer body. The inner body has a diameter less than a diameter of the outer body, which forms a cavity between the inner body and the outer body. The cavity is filled with an inert granular filler material. A first outer cap and a second outer cap cover respective ends of the outer body. A coupling is placed in fluid communication with the inner body and protrudes through the first outer cap. A tube is attached to the coupling protruding through the first outer cap to transfer a water sample to a sample collection site.

According to another embodiment of the present invention, there is provided a method of sampling pore water, including providing a pore water sampler having an elongated tubular outer body and an elongated tubular inner body within the outer body. The inner body has a diameter smaller than a diameter of the outer body to form a cavity between the inner body and the outer body. The cavity is filled with an inert granular filler material. A tube is connected to the sampler. A grid framework is provided on both the outer body and the inner body. The grid framework forms a plurality of perforations throughout an entire surface of the outer body and the inner body. The grid framework has raised and beveled sides that prevent blockage of the sampler by detritus as a sample is being collected. The sampler is buried in bottom sediment below surface water at a sample location and the tube is extended to a sample collection site. A vacuum is applied to the sampler to extract a sample through the tube to the sample collection site. The sampler is left buried under the surface water and subsequent samples are collected as needed from the same sample location.

According to another embodiment of the present invention, there is provided a method of assembling a pore water sampler, including providing an elongated tubular outer body, an elongated tubular inner body having a diameter less than a diameter of the outer body, an inner mesh, an outer mesh, a first inner cap, a second inner cap, a first outer cap, a second outer cap, a coupling, and a tube. A grid framework is provided on both the outer body and the inner body, the grid framework forming a plurality of perforations throughout an entire surface of the outer body and the inner body. The grid framework surrounding the perforations has raised and beveled sides that prevent blockage of the sampler by detritus as a sample is being collected. The inner mesh is wrapped around the inner body. The outer mesh is placed on an inner surface of the outer body. The coupling is connected to the first inner cap. The coupling has a first end and a tubing end opposite the first end. The tubing end of the coupling protrudes through an aperture in a top of the first inner cap. A first end of the inner body is covered with the first inner cap and a second end of the inner body is covered with the second inner cap to seal the inner body. The sealed inner body is inserted into a center of the outer body. An end of the outer body opposite the coupling is covered with the second outer cap. A space between the inner body and the outer body is filled with an inert granular filler material. A second end of the outer body opposite the first end is covered with the second outer cap. The tubing end of the coupling protrudes through an aperture in a top of the first outer cap. The tube is connected to the tubing end of the coupling and extended to a sample collection site.

BRIEF DESCRIPTION OF THE DRAWINGS

The above and other aspects and advantages of the present invention will become apparent and more readily appreciated from the following description, appended claims, and accompanying drawings, of which:

DESCRIPTION

Figure 1:
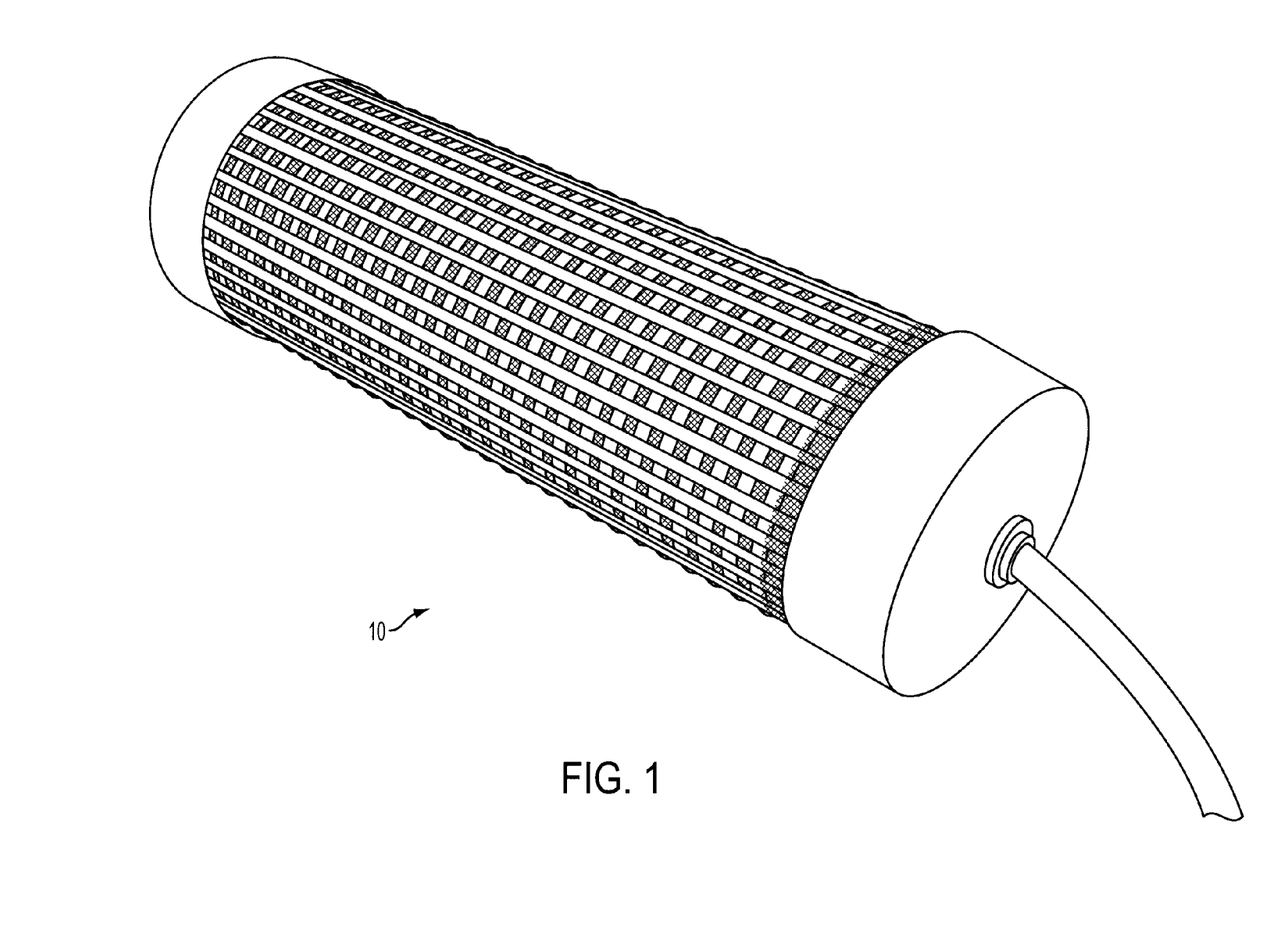
FIG. 1 illustrates a pore water sampler with tubing according to an embodiment of the present invention.
Figure 2:
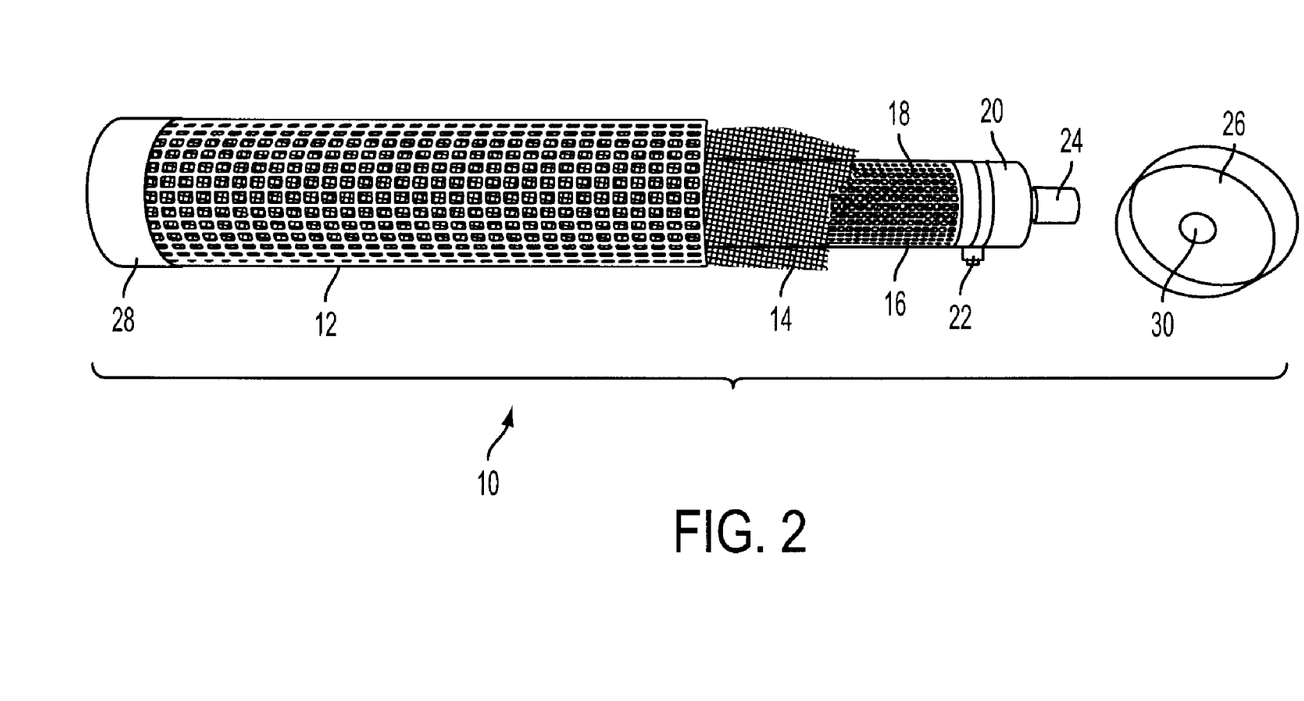
FIG. 2 illustrates a lengthwise, partially disassembled view of the pore water sampler of FIG. 1.

FIG. 1 illustrates a pore water sampler 10 according to one embodiment of the present invention. A lengthwise, partially disassembled view of the pore water sampler 10 is shown in FIG. 2. An outer perforated pipe 12, forming an outer screen, provides structural support and protection from abrasion during installation of the sampler 10. A first mesh 14 is located on the inner surface of the outer perforated pipe 12 and a second mesh 16 is wrapped around the outer surface of an inner perforated pipe 18, which forms an inner screen.

A bulkhead union 24 (also see FIG. 9) is inserted through an opening in a first inner cap 20. A nut 32 (see FIG. 3) is screwed onto the bulkhead union 24 to attach the bulkhead union 24 to the first inner cap 20. Referring to FIG. 2, the first inner cap 20 covers one end of the inner perforated pipe 18 and may be held in place by a fastener 22, such as a zip tie. A second inner cap 31 (see FIG. 4) covers the other end of the inner perforated pipe 18. A first outer cap 26 (FIG. 2) covers the outer perforated pipe 12 at the end adjacent to the bulkhead union 24. A second outer cap 28 covers an end of the outer perforated pipe 12 opposite the bulkhead union 24. The first outer cap 26 has an opening 30 through which the bulkhead union 24 extends.

Figure 5:
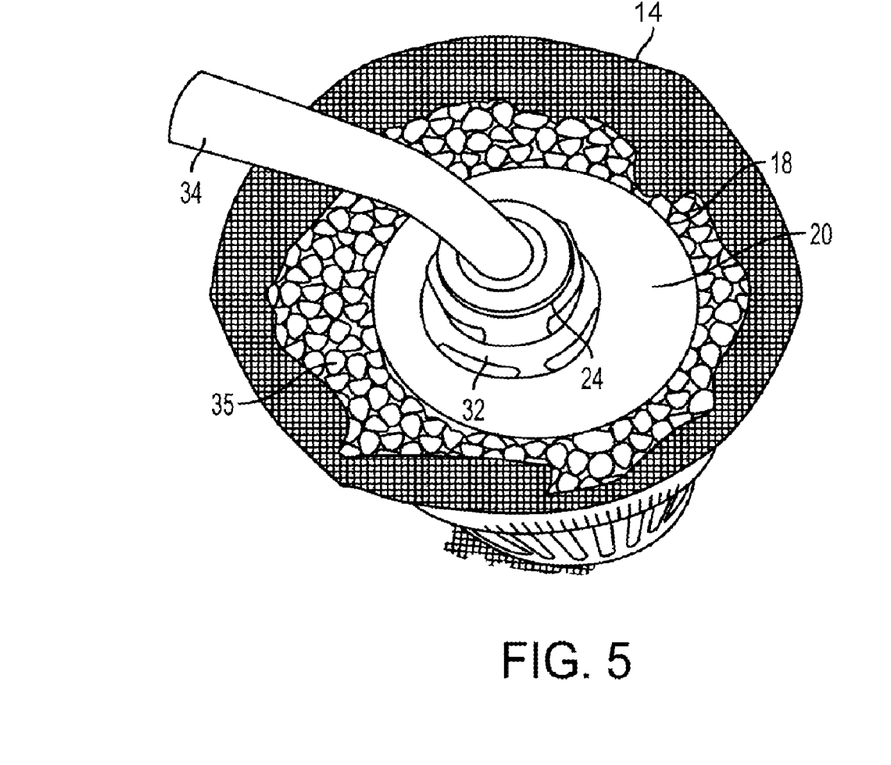
FIG. 5 illustrates an end view of the pore water sampler of FIG. 2 with the first outer cap removed to show a sand pack.

Tubing 34 (see FIG. 5) attaches to the bulkhead union 24 by, for example, being pushed into the bulkhead union 24. Other ways of attaching the tubing 34 are possible, including using screw-type fittings. The tubing 34 extends to the shoreline. FIG. 5 shows an end view of the pore water sampler 10 from the end containing the bulkhead union 24, with the first outer cap 26 removed. In FIG. 5, the inner perforated pipe 18 wrapped in the second mesh 16 extends lengthwise behind the first inner cap 20. An inert granular fill material 35, such as sand, is packed between the outer perforated pipe 12 and the inner perforated pipe 18, and is contained within the pore water sampler 10 by the first mesh 14, the second mesh 16, the first outer cap 26, and the second outer cap 28. The thickness of the sand pack 35 may be varied by changing the diameters of the outer perforated pipe 12 and the inner perforated pipe 18.

Figure 6:
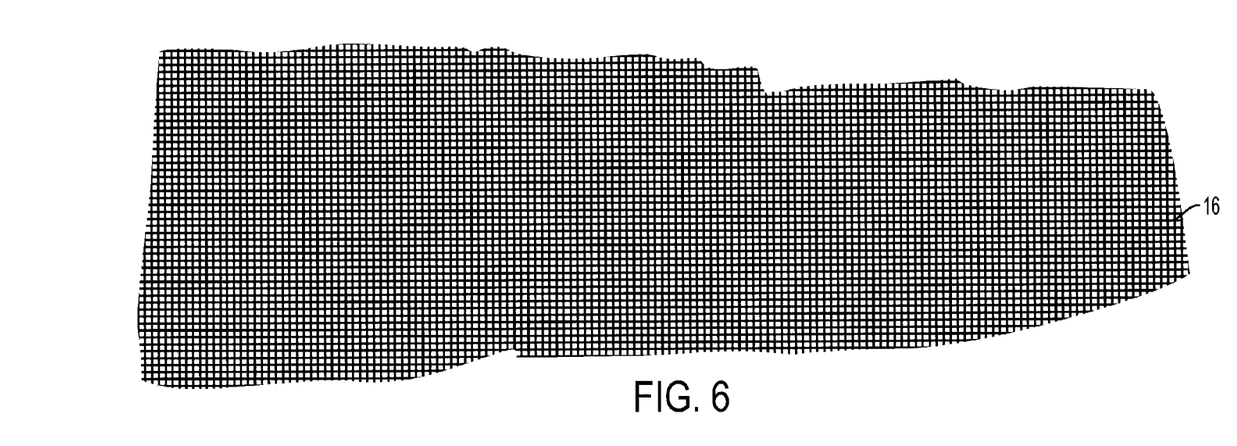
FIG. 6 illustrates a mesh for use with the pore water sampler of FIG. 2.

An example of a mesh sheet (e.g., the second mesh 16) is shown in FIG. 6. The first mesh 14 and the second mesh 16 are constructed of nylon or another inert substance, such as polypropylene, for example. The sizes of the mesh openings should not be larger than the grain size of the sand or granular fill material 35. The mesh openings can be less than 10 microns, but are preferably greater than about 10 microns to reduce clogging potential. The sizes of the mesh openings should be slightly smaller than the diameters of the granular fill 35, and the granular fill 35 should be sized to effectively limit transmittal of particulates in the size range of the site-specific deployment area. The first mesh 14 and the second mesh 16 can be attached to the outer perforated pipe 12 and the inner perforated pipe 18, respectively, with fasteners, such as zip ties, or can simply be held in place by the granular fill 35.

Figure 7A:
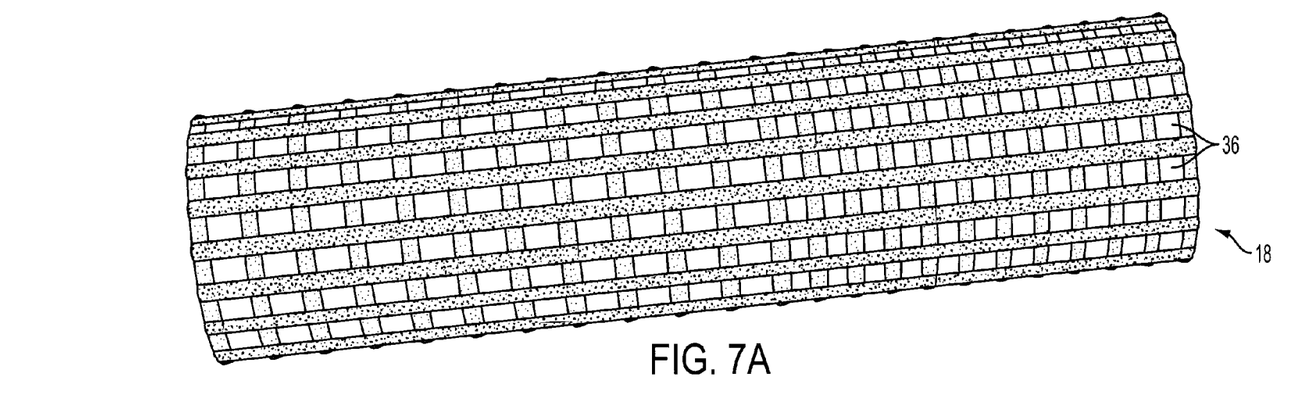
FIGS. 7A and 7B illustrate perforated pipes for use with the pore water sampler of FIG. 2.

An example of a perforated pipe (e.g., the inner perforated pipe 18) is shown in FIG. 7A. The diameter of the outer perforated pipe 12 ranges from about 1.5 inches to about 4 inches, and the length ranges from about 0.5 feet to about 3 feet. Preferably, the outer perforated pipe 12 is approximately 2.5 inches in diameter and about 0.7 feet in length. The length of the inner perforated pipe 18 is approximately the same as the length of the outer perforated pipe 12. The diameter of the inner perforated pipe 18 ranges from about 0.2 inches to about 1.5 inches, and preferably about 1.4 inches for a length of about 0.7 feet.

Figure 7B:
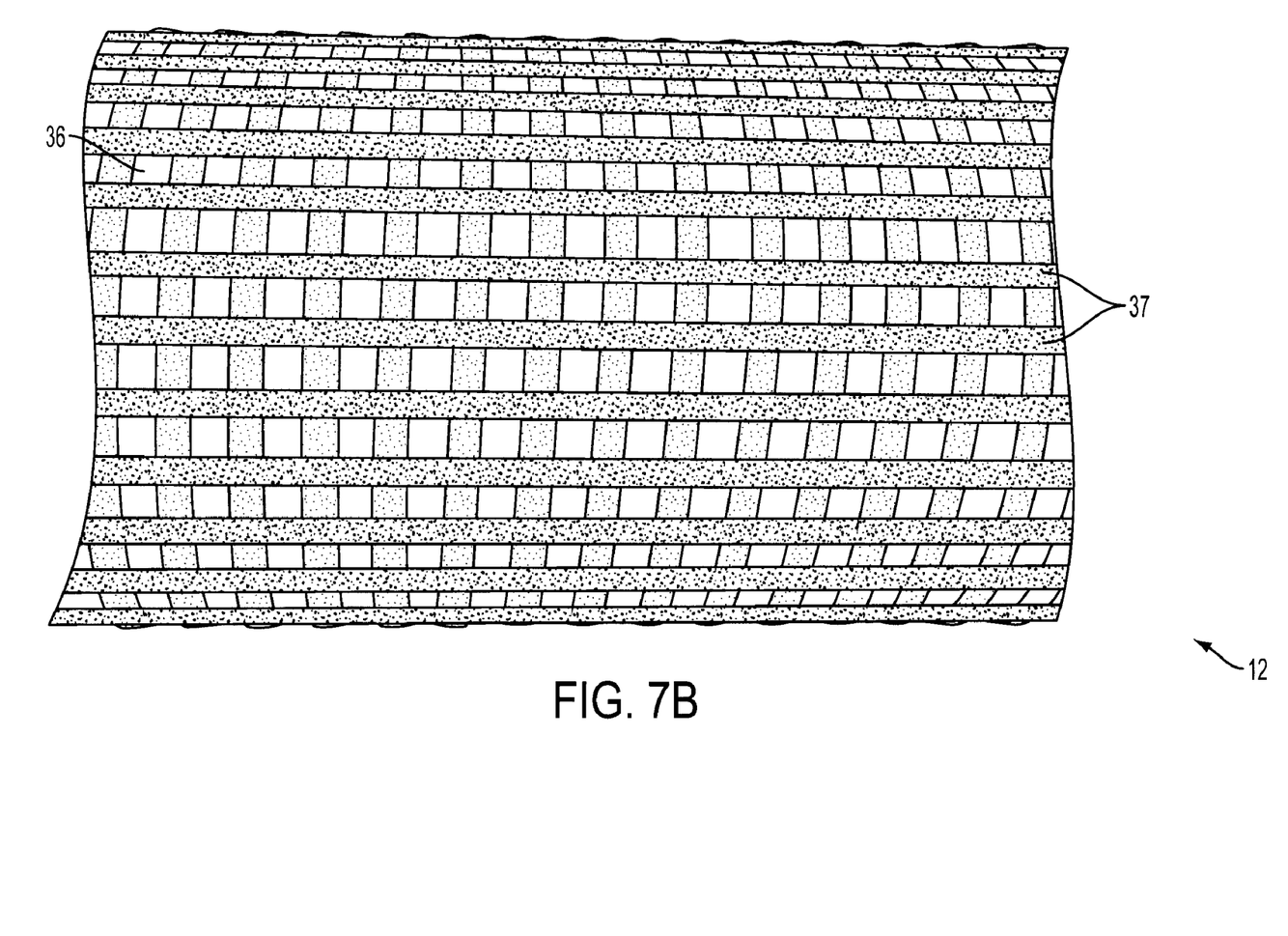
Figure 8A:
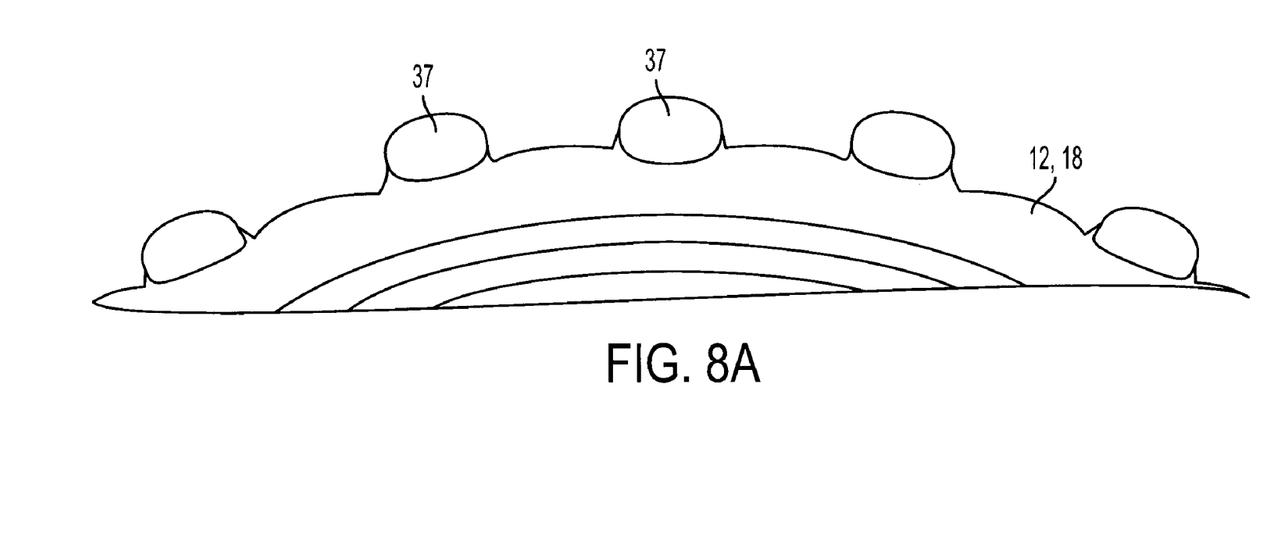
FIGS. 8A and 8B show close-up views of the perforated pipe of FIG. 7B to illustrate the raised framework surrounding the perforations.
Figure 8B:
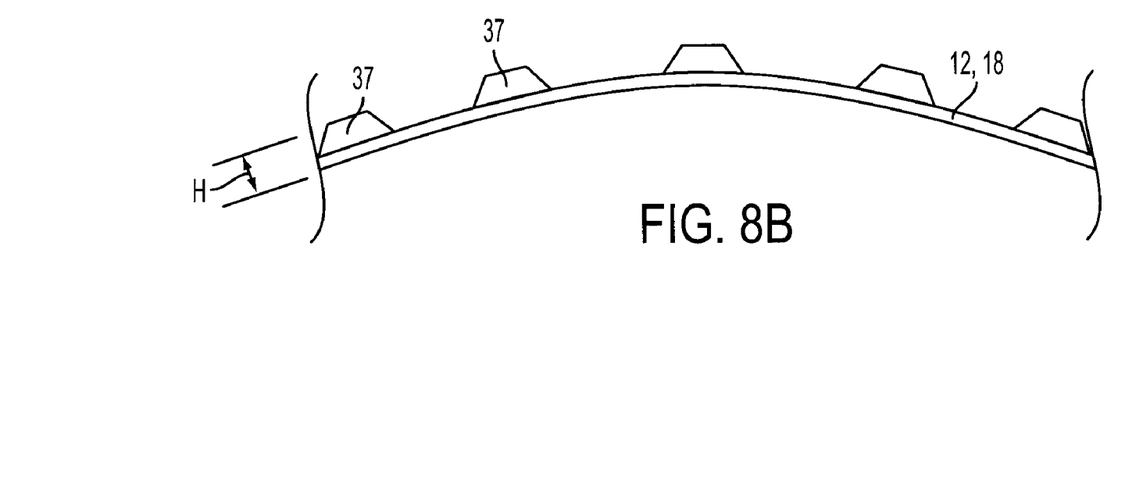

A close-up view of a perforated pipe (e.g., the outer perforated pipe 12) is shown in FIG. 7B. Both the outer perforated pipe 12 and the inner perforated pipe 18 contain perforations 36 throughout the entire structures. The perforations 36 are square-shaped, for example, and can have sides ranging from about 0.01 inches to about 0.50 inches. In the embodiment shown in FIG. 7B, the perforations 36 are about 0.015 inches by about 0.015 inches. The perforations 36 are surrounded by a grid framework with edges that are raised and preferably beveled. A close-up edge view of a pipe used to form either the outer perforated pipe 12 or the inner perforated pipe 18 is shown in FIGS. 8A and 8B to illustrate the raised, beveled framework surrounding the perforations 36. The grid framework includes elongated, parallel ridges 37 (also see FIG. 7B) that rise above the outer surface of the pipe 12, 18 to form an irregular outer surface. The irregular outer surface allows circuitous pathways of flow into the perforations 36 to counteract the potential for leaf debris to blanket and obstruct large parts of the outer perforated pipe 12. The height H of the ridges 37 may range from about 0.01 inches to about 0.2 inches. The sizes of the perforations 36 and the heights and shapes of the ridges 37 in the outer perforated pipe 12 and the inner perforated pipe 18, as well as the mesh sizes of the first mesh 14 and the second mesh 16, may vary as desired.

Figure 9:
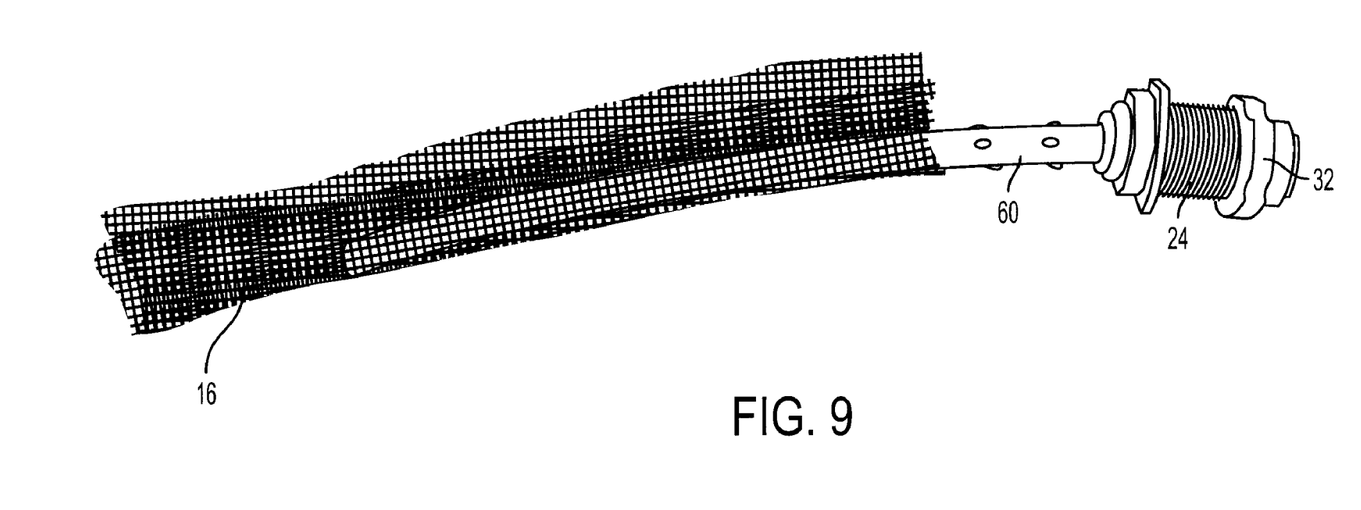
FIG. 9 illustrates a perforated tube wrapped in a mesh and attached to the bulkhead union, according to another embodiment of the present invention.

Rather than using the inner perforated pipe 18, a perforated tube 60 surrounded by the second mesh 16 may be used as the inner screen, as shown in FIG. 9. The sizes of the perforations in the perforated tube 60 may vary as desired. The perforations of the perforated tube 60 can be as small as will allow effective transmission of water and as large as will maintain structural integrity of the tube. The perforations of the tube 60 shown in FIG. 9 are approximately 0.1 inches in diameter. In the embodiment shown in FIG. 9, the perforated tube 60 attaches to one end of the bulkhead union 24, and the bulkhead union 24 attaches to the first outer cap 26. The diameter of the perforated tube 60 is about ¼-inch.

Following deployment, a peristaltic or other type of suction pump (not shown) is attached to the tubing 34 onshore, and the sampler 10 is pumped slowly to develop the sand pack 35. The suction induces water flow into the sampler 10 through the sand pack 35. The outer perforated pipe 12 limits potential blockage by sheet debris, such as leaf matter. The sand pack 35 reduces the amount of fine-grained material pumped from the sampler 10. After acceptably non-turbid water is observed in the pump discharge, the sampler 10 is left in place until the deployment disturbance re-equilibrates to ambient conditions. At the time the sample is collected, the peristaltic pump is attached to the tubing 34 at the shore and used to extract a sample by first purging the blank tubing 34 (typically, about a few hundred milliliters of water are purged) and sampling the water immediately following purging of the sampler 10. Following sample collection, the sampler 10 is left in place, where it can be used for subsequent sampling to provide long-term monitoring of the same location.

The pore water sampler 10 is buried in bottom sediment below surface water. There is not a limit to the distance from shore for the installation of the sampler 10. Longer distances simply mean that more tubing 34 will be used to extend to shore and a slightly longer pre-sample purge time would be needed. Because the peristaltic pump is limited to a lift of about 18 feet to about 20 feet, the discharge end of the sampler 10 on shore should be less than about 18 feet to about 20 feet above the water surface. Deployment of the sampler 10 in deep water may require the use of divers or other remote installation methods.

Figure 3:
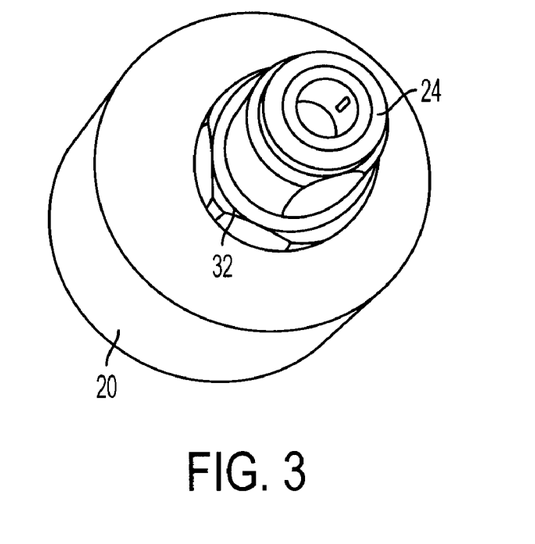
FIG. 3 illustrates a first inner cap with a bulkhead union attached for use with the pore water sampler of FIG. 2.
Figure 4:
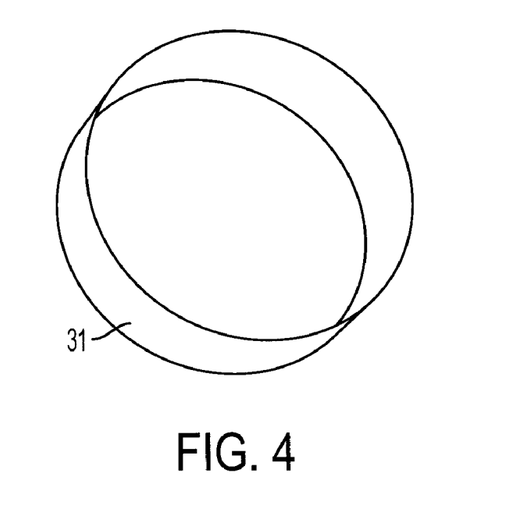
FIG. 4 illustrates a second inner cap for use with the pore water sampler of FIG. 2.

Various types of plastics may be used to construct any part of the sampler 10, such as polyethylene, polyurethane, Teflon®, as well as other non-metal materials. The nut 32 shown in FIGS. 3, 5, and 9 is constructed of stainless steel, but it is in a position that is distant from the flow-through areas of the sampler 10. The nut 32 may also be constructed of plastic.

Figure 10:
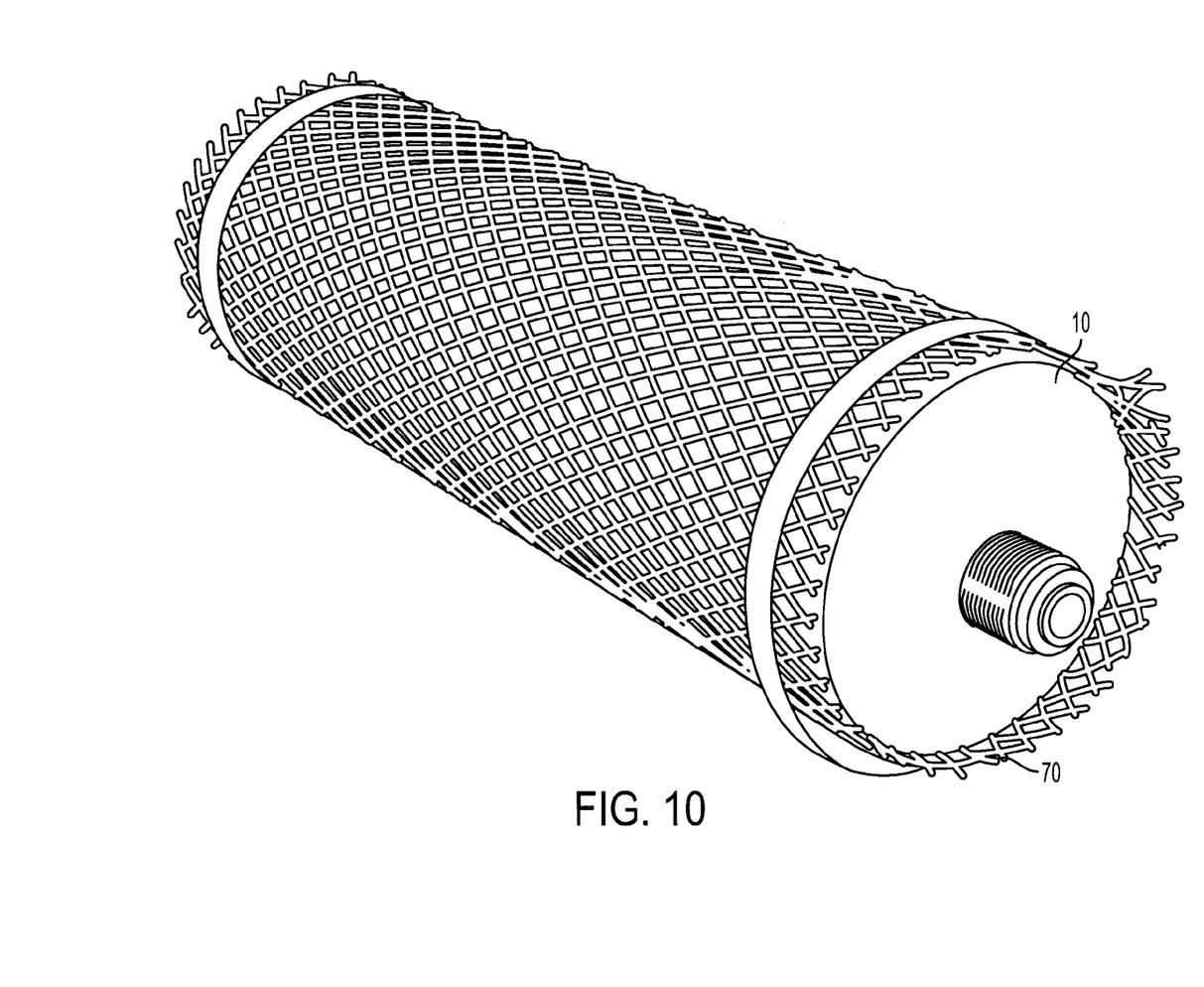
FIG. 10 illustrates the pore water sampler of FIG. 1 covered with a mesh sleeve.
Figure 11:
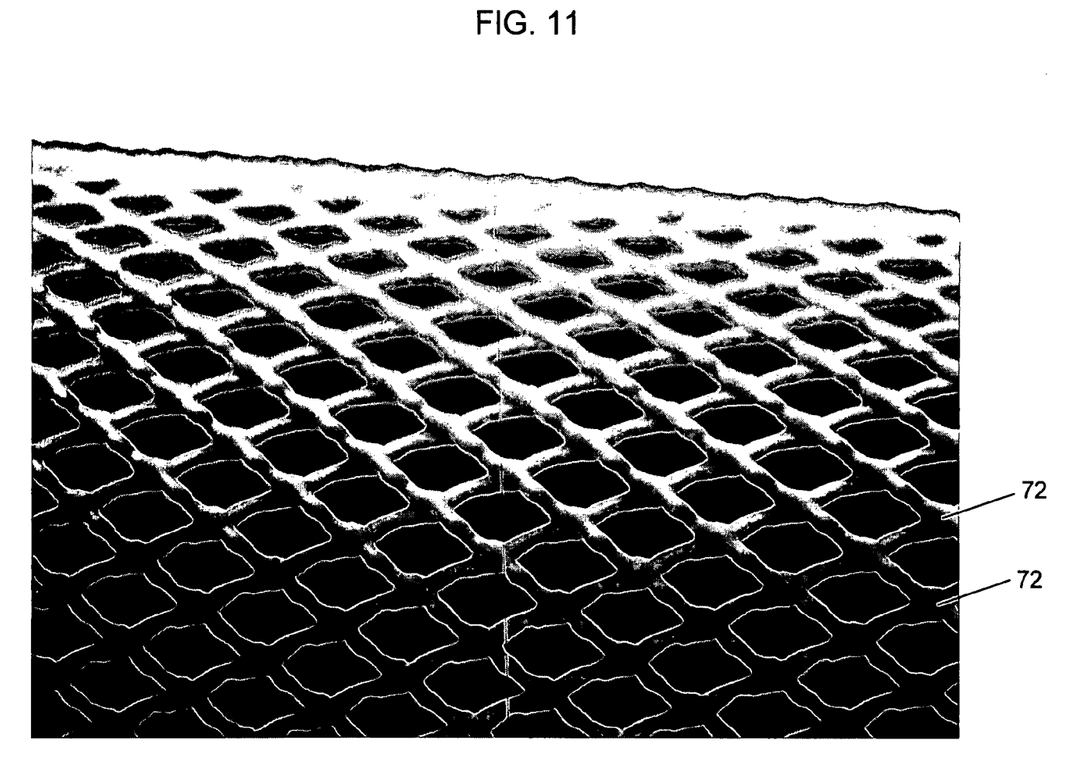
FIG. 11 illustrates a close-up view of the mesh sleeve of FIG. 10.

According to another embodiment of the present invention, the outer surface of the sampler 10 may be covered with a mesh sleeve 70, as shown in FIG. 10. This layering of mesh and pipe openings or perforations decreases the potential for clogging by large matter. The mesh sleeve 70 may be constructed of flexible plastic with raised ridges 72, as shown in the close-up view of the mesh sleeve 70 in FIG. 11.

The present invention has advantages over existing diffusion sampler technology. The present invention allows pore water samples to be collected from the same location indefinitely, as long as sufficient time elapses between sampling events for the ambient water to return to prepumped conditions. Also, there is no need to refill the sampler 10 with any kind of water because it is self filling with ambient formation water.

The present invention also has advantages over existing prepacked well screens. The present invention does not need a standpipe that extends to the surface. Instead, water is extracted from the sampler 10 through the tubing 34 that runs from the sampler 10 to the shoreline, where samples can be collected using the peristaltic pump without the need for a boat.

Parameters of interest in pore water investigations may be adversely affected by stainless steel. In the present invention, the outer perforated pipe 12 does not need to be constructed of stainless steel to withstand deployment abrasion. The rigid outer perforated pipe 12 of the sampler 10 protects the first mesh 14 and the second mesh 16 from abrasion. This allows less expensive construction materials to be used. The nut 32 on the outside of the sampler 10 that attaches the bulkhead union 24 to the sampler 10 can be constructed of plastic. Even if the nut 32 is constructed of stainless steel, the nut 32 is in a position that is distant from the flow-through areas of the sampler 10. Thus, in the present invention, stainless steel is not part of the sampler 10 that is in intimate contact with sampled water.

In addition, the present invention differs from existing technology in that the outer perforated pipe 12 contains perforations 36 throughout the entire structure. The perforations 36 are large relative to existing technology. In addition, the edges of the perforations are beveled and raised. The size of the perforations 36 and the raised, beveled borders of the perforations 36 present an irregular outer surface that allows circuitous pathways of flow into the ports to counteract the potential for leaf debris to blanket and obstruct large parts of the outer perforated pipe 12. The sand pack 35 within the outer perforated pipe 12 further excludes organic debris from the sampler 10 and allows the sampler 10 to be used effectively both in the leaf-litter environment of bottom sediment and in more sandy sediments.

The present invention is a stand-alone, pre-packed pore water sampler having a small-diameter tubing that connects the sampler to the shore. The sampler is constructed almost entirely of plastic and polymers, making it substantially less expensive than prepacked screens constructed of stainless steel. The sampler also has no stainless steel in intimate contact with water movement, minimizing potential chemical effects that can be associated with stainless-steel well screens. The outer layer is a rigid plastic perforated pipe with a raised framework to counter the potential blockage effects of sheet debris, such as leaf matter.

It will be appreciated by those skilled in the art that modifications and variations of the present invention are possible without departing from the principles and spirit of the invention, the scope of which is defined in the appended claims and their equivalents.

GENERAL BIBLIOGRAPHY ON THE SUBJECT

1. Church, P. E., Vroblesky, D. A., Lyford, F. P., and Willey, R. E., 2002, Guidance on the use of passive-vapor-diffusion samplers to detect volatile organic compounds in groundwater-discharge areas, and example applications in New England: U.S. Geological Survey Water-Resources Investigations Report 02-4186, 79 p.
2. Imbrigiotta, T. E., Ehlke, TA., and Lacombe, P. J., 2002, Comparison of dialysis membrane diffusion samplers and two purging methods in bedrock wells: Paper 1D-02, in: A. R. Gavaskar and A. S. C. Chen (Eds.), *Remediation of Chlorinated and Recalcitrant Compounds*—2002. Proceedings of the Third International Conference on Remediation of Chlorinated and Recalcitrant Compounds (Monterey, Calif.; May 2002). ISBN 1-57477-132-9, published by Battelle Press, Columbus, Ohio, www.battelle.org/bookstore.
3. Jacobs, P. H., 2002, A new rechargeable dialysis pore water sampler for monitoring sub-aqueous in-situ sediment caps: Water Research, v. 36, p. 3121-3129.
4. Karp, K. E., 1993, A diffusive sampler for passive monitoring of underground storage tanks: *Ground Water Monitoring & Remediation* 13, no 1:101-106.
5. Namieśnik, Jacek, Zabigala, Bożena, Kot-Wasik, Agata, Partyka, Monika, and Wasik, Andrzej, 2005, Passive sampling and/or extraction techniques in environmental analysis: a review: Analytical and Bioanalytical Chemistry, v. 381, p. 279-301.
6. Bjerg. P. L., Jakobsen, R., Bay, H., Rasmussen, M., Hans-Jørgen, A., and Christensen, TH., 1997, Effects of well construction on H2 measurements made for characterization of redox conditions in a contaminated aquifer: Environmental Science and Technology, v. 31, no. 10, p. 3029-3031.
7. Paludan and Morris, 1999, Distribution and speciation of phosphorus along the salinity gradient in intertidal marsh sediments: Biogeochemistry, v. 45, p. 197-221.
8. Vroblesky, D. A., and Hyde; W. T, 1997, Diffusion samplers as an inexpensive approach to monitoring VOCs in ground water: Ground Water Monitoring and Remediation, vol. 17, no. 3, pp. 177-184.
9. Vroblesky, D. A., Lorah, M. M., and Trimble, S. P. 1991. Mapping zones of contaminated ground-water discharge using creek-bottom-sediment vapor samplers, Aberdeen Proving Ground Md. *Ground Water*. vol 29. no. 1. p. 7-12.
10. Vroblesky, D. A., 2001a, User's guide for polyethylene-based passive diffusion bag samplers to obtain volatile organic compound concentrations in wells: Part 1: Assembly and quality control and assurance: U.S. Geological Survey Water Resources Investigations Report 01-4060, 18 p.
11. 2001b, User's guide for polyethylene-based passive diffusion bag samplers to obtain volatile organic compound concentrations in wells: Part 2: Field tests: U.S. Geological Survey Water Resources Investigations Report 014061, 102 p.
12. Vroblesky, D. A., 2002a, Part 1. Guidance on the use of passive-vapor-diffusion samplers: in Church, PE., Vroblesky, D. A., Lyford, F. R, and Willey, R. E., Guidance on the use of passive-vapor-diffusion samplers to detect volatile organic compounds in ground-water-discharge areas, and example applications in New England: U.S. Geological Survey Water-Resources Investigations Report 02-4186, 79 p.
13. 2002b, Laboratory and field testing of passive vapor-diffusion sampler equilibration times, temperature effects, and sample stability: in Church, P E., Vroblesky, D. A., Lyford, F. P., and Willey, R. E., Guidance on the use of passive-vapor-diffusion samplers to detect volatile organic compounds in ground-water-discharge areas, and example applications in New England: U.S. Geological Survey Water-Resources Investigations Report 02-4186, 79 p.
14. Vroblesky, D. A., Petkewich, M. D., and Campbell, TR., 2002a, Field tests of diffusion samplers for inorganic constituents in wells and at a ground-water-discharge zone: U.S. Geological Survey Water Resources Investigation Report 024031, 24 p.
15. Vroblesky, D. A., Petkewich, M. D., and Campbell, T. R., 2002b, Considerations for sampling inorganic constituents in ground water using diffusion samplers: in, Gavaskar, A. R., and Chen, A. S. C. (eds.), Remediation of Chlorinated and Recalcitrant Compounds, Proceedings of the Third International Conference on Remediation of Chlorinated and Recalcitrant Compounds, Monterey, Calif., May 2002, 1F-05.
16. Geoprobe Systems, 601 N. Broadway, Salina, Kans. 67401, <http://www.geoprobe.com/products/tools/gw_monitoring/well_menu.htm>
17. Johnson Screens (India) Ltd., Parisram' 5-B Rashmi Society, Mithakhali Circle, Navrangapura, Ahmedabad-380 009, Gujarat, India, <http://iohnsonfiltrationindia.com/other_imp_oil_screen.htm>
18. Weatherford International Ltd., 515 Post Oak Blvd., Suite 600, Houston, Tex. 77027, <http://www.weatherford.com/weatherford/groups/public/documents/completion/cmp_wel lscreens.hcsp>
19. Baker Hughes Inc., 3900 Essex Lane, Suite 1200, Houston Tex. 77027-5177<http://www.bakerhughes.com/bot/coiled_tubing/pdfs/scs_pg31__37.pdf>
20. Schlumberger Limited, 153 East 53 Street, 57th Floor, New York, N.Y. 10022, <http://www.oilfield.sib.com/media/services/completion/sand/formation_isolation_valve.p df>
21. Ministry of Environment, Environmental Protection Division, Environmental Management Branch, British Columbia, PO Box 9339, Stn Prov Govt, Victoria BC V8W 9M1, <http://www.env.gov.bc.ca/epd/>

What is claimed is:

1. A device for sampling water, comprising:
    an elongated tubular outer body having a grid framework forming a plurality of perforations throughout the entire outer body, the grid framework surrounding the perforations having raised sides;
    an elongated tubular inner body contained within the outer body, the inner body having perforations and a diameter less than a diameter of the outer body to form a cavity between the inner body and the outer body, the cavity being filled with a granular filler;
    a first outer cap and a second outer cap covering respective ends of the outer body;
    a coupling in fluid communication with the inner body and protruding through the first outer cap; and
    a tube attached to the coupling protruding through the first outer cap to transfer a water sample to a sample collection site.

2. The device of claim 1, wherein the grid framework comprises a plurality of parallel ridges extending a length of the outer body, the ridges rising above an outer surface of the outer body to form an irregular outer surface.

3. The device of claim 2, wherein each ridge has beveled sides and has a height ranging from about 0.01 inches to about 0.2 inches.

4. The device of claim 1, wherein each perforation is square-shaped and has sides ranging from about 0.01 inches to about 0.50 inches in length.

5. The device of claim 1, wherein the inner body has a grid framework forming a plurality of perforations throughout the entire inner body, the grid framework surrounding the perforations having raised sides.

6. The device of claim 1, further comprising:
    an outer mesh extending along an inner surface of the outer body and an inner mesh wrapped around an outer surface of the inner body, the granular filler being placed in the cavity between the inner mesh and the outer mesh; and
    a first inner cap and a second inner cap, the first inner cap covering a first end of the inner body and the second inner cap covering a second end of the inner body opposite the first end of the inner body, the coupling being connected to the first inner cap and protruding from the first inner cap.

7. The device of claim 6, wherein the outer mesh and the inner mesh are constructed of an inert material.

8. The device of claim 7, wherein the inert material is one of nylon and polypropylene.

9. The device of claim 6, wherein each of the outer body, the inner body, the coupling, the first inner cap, the second inner cap, the first outer cap, and the second outer cap are constructed of an inert plastic material.

10. The device of claim 9, wherein the inert plastic material is one of polyethylene, polyurethane, and Teflon®.

11. The device of claim 1, wherein the diameter of the outer body ranges from about 1.5 inches to about 4 inches, the length of the outer body ranges from about 0.5 feet to about 3 feet, the diameter of the inner body ranges from about 0.2 inches to about 1.5 inches, and the length of the inner body is approximately the same length as the outer body.

12. The device of claim 11, wherein the outer body and the inner body are pipes, and wherein the diameter of the outer body is about 2.5 inches, the length of the outer body is about 0.7 feet, the diameter of the inner body is about 1.4 inches, and the length of the inner body is about 0.7 feet.

13. The device of claim 1, wherein the granular filler is sand.

14. The device of claim 1, wherein the inner body is a perforated tube wrapped in a mesh and has a diameter of about 0.25 inches.

15. The device of claim 14, wherein the coupling is in fluid communication with the perforated tube.

16. The device of claim 1, wherein an outer surface of the device is covered with a mesh sleeve.

17. A method of sampling pore water, comprising:
providing a pore water sampler comprising an elongated tubular outer body and an elongated tubular inner body within the outer body, the inner body having a diameter smaller than a diameter of the outer body to form a cavity between the inner body and the outer body, filling the cavity with a granular filler, and connecting a tube to the sampler;
providing a grid framework on both the outer body and the inner body, the grid framework forming a plurality of perforations throughout an entire surface of the outer body and the inner body, the grid framework surrounding the perforations having raised sides that prevent blockage of the sampler by detritus as a sample is being collected;
burying the sampler in bottom sediment below surface water at a sample location and extending the tube to a sample collection site;
applying a vacuum to the sampler to extract a sample through the tube to the sample collection site; and
leaving the sampler buried under the surface water and collecting subsequent samples as needed from the same sample location.

18. A method of assembling a pore water sampler, comprising:
providing an elongated tubular outer body, an elongated tubular inner body having a diameter less than a diameter of the outer body, an inner mesh, an outer mesh, a first inner cap, a second inner cap, a first outer cap, a second outer cap, a coupling, and a tube;
providing a grid framework on both the outer body and the inner body, the grid framework forming a plurality of perforations throughout an entire surface of the outer body and the inner body, the grid framework surrounding the perforations having raised and beveled sides that prevent blockage of the sampler by detritus as a sample is being collected;
wrapping the inner mesh around the inner body;
placing the outer mesh around an inner surface of the outer body;
connecting the coupling to the first inner cap, the coupling having a first end and a tubing end opposite the first end, the tubing end of the coupling protruding through an aperture in a top of the first inner cap;
covering a first end of the inner body with the first inner cap and a second end of the inner body with the second inner cap to seal the inner body;
inserting the sealed inner body into a center of the outer body;
covering an end of the outer body opposite the coupling with the second outer cap;
filling a space between the inner body and the outer body with a granular filler;
covering a second end of the outer body opposite the first end with the second outer cap, the tubing end of the coupling protruding through an aperture in a top of the first outer cap; and
connecting the tube to the tubing end of the coupling and extending the tube to a sample collection site.

19. The method of claim 18, wherein said providing a grid framework on the outer body comprises providing a plurality of parallel ridges extending a length of the outer body, the ridges rising above an outer surface of the outer body to form an irregular outer surface.

20. The method of claim 18, further comprising constructing the sampler of an inert plastic material.

\* \* \* \* \*